US008871499B2

(12) United States Patent
Tschumperlin et al.

(10) Patent No.: US 8,871,499 B2
(45) Date of Patent: Oct. 28, 2014

(54) MULTI-WELL CULTURE PLATE COMPRISING GELS WITH DIFFERENT SHEAR MODULUS

(75) Inventors: Daniel Tschumperlin, Norfolk, MA (US); Fei Liu, Cambridge, MA (US); Justin Mih, Mission Hill, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1263 days.

(21) Appl. No.: 12/675,839

(22) PCT Filed: Aug. 28, 2008

(86) PCT No.: PCT/US2008/010202
§ 371 (c)(1),
(2), (4) Date: Jan. 6, 2011

(87) PCT Pub. No.: WO2009/032164
PCT Pub. Date: Mar. 12, 2009

(65) Prior Publication Data
US 2011/0104798 A1    May 5, 2011

Related U.S. Application Data

(60) Provisional application No. 60/969,104, filed on Aug. 30, 2007, provisional application No. 60/970,778, filed on Sep. 7, 2007.

(51) Int. Cl.
*C12M 3/00* (2006.01)
*C12Q 1/02* (2006.01)
*C12Q 1/04* (2006.01)

(52) U.S. Cl.
USPC .......... 435/288.4; 435/305.2; 435/29; 435/34

(58) Field of Classification Search
CPC ........ C12M 23/12; C12M 25/00; C12Q 1/02; C12Q 1/025; C12Q 1/04; C12N 5/06; C12N 11/02; C12N 11/08; C12N 11/12
See application file for complete search history.

(56) References Cited

U.S. PATENT DOCUMENTS

| | | | |
|---|---|---|---|
| 5,217,899 A | | 6/1993 | Shapiro et al. |
| 5,244,799 A | * | 9/1993 | Anderson .................... 435/397 |
| 5,706,696 A | | 1/1998 | Wagner |
| 6,037,141 A | | 3/2000 | Banes |
| 6,057,150 A | | 5/2000 | Lee et al. |
| 6,586,235 B1 | | 7/2003 | Banes |
| 6,897,064 B2 | * | 5/2005 | Yoshioka et al. ............ 435/397 |
| 7,160,687 B1 | | 1/2007 | Kapur et al. |
| 7,902,121 B2 | * | 3/2011 | Chen et al. ....................... 506/4 |
| 7,988,685 B2 | * | 8/2011 | Ziaie et al. .................. 604/890.1 |
| 2004/0014078 A1 | | 1/2004 | Xia et al. |
| 2006/0035325 A1 | | 2/2006 | Crabtree et al. |
| 2006/0110822 A1 | | 5/2006 | Robbins et al. |
| 2007/0026518 A1 | * | 2/2007 | Healy et al. ................... 435/325 |
| 2007/0128174 A1 | | 6/2007 | Kleinsek et al. |

FOREIGN PATENT DOCUMENTS

WO    WO-2005007796    1/2005

OTHER PUBLICATIONS

Discher, et al. "Tissue Cells Feel and Respond to the Stiffness of their Substrate", Science, 310:1139-1143 (2005).
Engler, et al. "Matrix Elasticity Directs Stem Cell Lineage Specification", Cell, 126:677-89 (2006).
Fulmer, et al. "Morphologic-Physiologic Correlates of the Severity of Fibrosis and Degree of Cellularity in Idiopathic Pulmonary Fibrosis", The Journal of Clinical Investigation, 63:665-676 (1979).
Linder-Ganz, et al. "Mechanical Compression-Induced Pressure Sores in Rat Hindlimb: Muscle Stiffness, Histology, and Computational Models", J Appl Physiol, 96:2034-49 (2004).
Lo, et al. "Cell Movement is Guided by the Rigidity of the Substrate", Biophysical Journal, 79:144-152 (2000).
Rehfeldt, et al. "Cell Responses to the Mechanochemical Microenvironment-Implications for Regenerative Medicine and Drug Delivery", Adv Drug Deliv Rev., 59:1329-39 (2007).
Semler, et al., "Engineering Hepatocellular Morphogenesis and Function Via Ligand-Presenting Hydrogels with Graded Mechanical Compliance", Biotechnol and Bioeng., 89(3):296-307 (2005).
Trepat, et al. "Universal Physical Responses to Stretch in the Living Cell", Nature, 447:592-596 (2007).
Wellman, et al. "Breast Tissue Stiffness in Compression is Correlated to Histological Diagnosis", Harvard BioRobotics Laboratory Technical Report, Harvard University, Cambridge, Mass, USA (1999).
Wang, et al. "Preparation of a Flexible, Porous Polyacrylamide Substrate for Mechanical Studies of Cultured Cells", Methods in Enzymology, 298:489-496, 1998.
Wong, et al. "Directed Movement of Vascular Smooth Muscle Cells on Gradient-Compliant Hydrogels", Langmuir, 19(5):1908-1913 (2003).
Yeung, et al. "Effects of Substrate Stiffness on Cell Morphology, Cytoskeletal Structure, and Adhesion", Cell Motility and the Cytoskeleton, 60:24-34 (2005).

* cited by examiner

*Primary Examiner* — David M Naff
(74) *Attorney, Agent, or Firm* — Mintz Levin Cohn Ferris Glovsky and Popeo, P.C.

(57) ABSTRACT

A multi-well plate can be loaded with a range of compliant substrates. Commerically-available assays can be used to test cellular responses across a plate with shear modulus from 50 to 51200 Pascals. Cells can be grown in the plates, and can be manipulated and analyzed. Hydrogels can be attached to the bottom of a well. The plates can support the attachment and growth of different cell types and can be compatible with standard 96-well and 384-well plate assays. The mechanical properties of the hydrogels can be reproducible and stable to increase the shelf life of the substrate. The hydrogel can be compatible with growth of a variety of cell types, various attachment ligands such as collagen I, collagen IV, fibronectin, vitronectin, laminin, or RGD peptides and can be coupled to the gel surface.

16 Claims, 11 Drawing Sheets

MULTI-WELL CULTURE PLATE COMPRISING GELS WITH DIFFERENT SHEAR MODULUS

CROSS-REFERENCE TO RELATED ACTIONS

This application is a national phase entry of International Application No. PCT/US08/10202, filed on Aug. 28, 2008, which claims the benefit of U.S. Provisional Application No. 60/970,778, filed on Sep. 7, 2007, and claims the benefit of U.S. Provisional Application No. 60/969,104, filed on Aug. 30, 2007.

GRANTS

The government has certain rights to the present invention under contract NIH HL-82856, GM-073628.

BACKGROUND

The physical environment of a living cell influences its ability to proliferate, metabolize, differentiate and remodel. Living cells specify lineage and express different phenotypic and physical states with extreme responsiveness to stiffness (i.e., shear modulus) of their underlying matrix.

A general consensus is emerging among bioengineers and life scientists that rigid substrates may, in many cases, be inappropriate for assessing cell behaviors. Early efforts to more realistically mimic the tissue environment relied on three dimensional reconstituted biological components that form hydrogels, such as collagen, fibrin, and Matrigel. More recently, synthetic, self-assembling peptide gels (PuraMatrix), alginate sponges (AlgiMatrix), and hyaluronan-derived gels (Glycosan) have become commercially available. However, these methods can be prohibitively costly, technologically impractical, or incompatible with many cell-based high-throughput assays, which are designed with 2-D systems in mind. And while culture in three dimensions is appreciated, in general, these systems do not allow wide control of elasticity. Further, in many cases, cell responses to pharmaceutical compounds and biologics in vitro do not accurately predict in vivo functionality and toxicity.

SUMMARY

In accordance with implementations of the invention, one or more of the following capabilities may be provided. A collection of wells with varying shear modulus (i.e., stiffness) can be provided. In an embodiment, a multi-well plate can be fabricated with a range of compliant substrates. Commerically-available or custom-made assays can be used to test cellular responses across a plate with stiffness ranging from 50 to 150,000 Pascals. For example, lung fibroblast proliferation and apoptosis which can be strongly dependent upon substrate shear modulus can be tested. Cells can be grown in the plates, and can be manipulated and analyzed in a manner consistent with conventional multi-well plates.

In an embodiment, hydrogels can be affixed (i.e., firmly attached) to the bottom of a well (e.g., wells in 24, 96, 384 well plates). The firm attachment enables long-term cell cultures, as well as compatibility with some assay reagents that may cause the hydrogels to shrink and detach. The plates can support the attachment and growth of different cell types and can be compatible with standard multi-well plate assays. The mechanical properties of the hydrogels can be reproducible and stable to increase the shelf life of the substrate. The hydrogel can be compatible with growth of a variety of cell types, various attachment ligands such as collagen I, collagen IV, fibronectin, vitronectin, laminin, or RGD peptides and can be coupled to the gel surface.

Multiple shear modulus gels, varying in orientation, can be casted and derivatized in a multi-well glass-bottom plate. Stiffness-dependent biology can be assessed in a high-throughput manner and subject to a standard multi-well plate assay, including but not limited to, cell proliferation, apoptosis, signaling events, and detection of soluble and insoluble factors. Cells grown in the multiple shear modulus plate can be fixed and immunologically stained, or isolated for gene expression and protein analysis. Attachment-dependent cell types can be conceivably studied, including fibroblasts, smooth muscle, endothelial, epithelial, tumor, osteoid, and neuronal. The plate can serve as a tool to direct the differentiation of adult or embryonic stem cells.

The devices and methods described herein are useful to program or reprogram embryonic and/or adult stem cells, e.g., the latter being obtained from normal or tumor-derived tissue. The cells are cultured in the chamber and can be subjected to variations in stiffness of the substrate. Reprogrammed stem cells are identified by their behavior (e.g., movement or lack thereof), physical state of the cytosol, appearance, change in gene/protein expression, or elaboration of intracellular or secreted factors, among other parameters. The methods and imaging systems are used to monitor characteristics of cells and identify/screen for cells of a desired phenotype, e.g., cells at a desired state of differentiation or "sternness", e.g., phenotype as a response to variations in changes of stiffness of culture substrate applied to a cell or plurality of cells. The methods include non-invasive, non-perturbing, automatable, and quantitative methods and are applied to the examination of cells such as adult or embryonic stem cells as well as differentiated cells of all phenotypes and to cells at various stages of differentiation. Viability, sternness, or plasticity of the cell, in response to the culture environment or physical stresses to which the cell or cells are exposed are monitored and quantified at various points during culture, as preserved/fixed, or in real time.

In general, in an aspect, the invention provides a method for fabricating hydrogels with elastic properties covering a physiological range, including placing a first polymerizing solution into a well, covering the first polymerizing solution with a plate, such that the area of the plate is less than the area of the well, conjugating the first polymerizing solution with a ligand, placing a second polymerizing solution into the well, such that oxygen in the air substantially inhibits polymerization at the air-liquid interface; and detoxifying the well.

Implementations of the invention may include one or more of the following features. The uniformity of ligand binding can be assessed with anti-ligand and anti-IgG-coated fluorescent beads. The second polymerizing solution can be distributed evenly by tapping the well. The second polymerizing solution can substantially cover a ring shaped area defined by the edge of the first polymerizing solution and the well. The second polymerizing solution can affix the first polymerizing solution to the well.

In general, in another aspect, the invention provides an apparatus including a well, a dispensing system configured to deliver a polymerization solution to the well, a peg configured to be inserted into the well, and a glass plate disposed at the distal end of the peg, such that the area of the glass plate is less than the area of the well and is configured to contact the polymerization solution in the well.

Implementations of the invention may include one or more of the following features. The well can be a well in a multi-well plate, and the peg can be a more than one peg, such that each of the pegs can be configured to be inserted into a corresponding well in the multi-well plate. A peg insertion system can be configured to move the peg into and out of the well. A second dispensing system can be configured to deliver a second polymerization solution into the well. The dispensing system can configured to deliver the second polymerization solution into the well. The well can be a 96 or 384 well plate. A well plate stage can be configured to move the well in at least one axis. A well tapper can be configured to tap the well.

In general, in another aspect, the invention provides an apparatus including a multi-well plate, a first gel affixed in at least a first well in the plate, and a second gel affixed in at least a second well in the plate, such that the shear modulus of the first and second gels are different.

Implementation of the invention may include one or more of the following features. A third gel can be disposed in at least a third well of the plate, such that the shear modulus of the first, second, and third gels are different from one another. The wells can be disposed on the plate in columns and the shear modulus of the gels in the wells in a column can be substantially the same. The multi-well plate can be a 96 well plate, and can include 12 columns of wells such that one column of wells is empty and 11 columns of wells contain gel, whereby the gels in a well of a column can have a substantially similar shear modulus to the gels in wells of the same column.

In general, in another aspect, the invention provides an apparatus including a multi-well plate, a gel affixed in at least a first well in the plate, wherein the thickness of the gel is less than 1 millimeter.

Implementations of the invention may include one or more of the following features. The thickness of the gel can be less than 100 microns. A second gel can be disposed in at least a second well in the plate, such that the thickness of the second gel is less than 1 millimeter, and the shear modulus of the first and second gels are different. The thickness of the second gel can be less than 100 microns. The gel can be derivatized with a heterobifunctional crosslinker and a ligand.

Also within the invention is a method of simulating a physiological growth condition by contacting a cell with the device or apparatus. For example, the cell is a cardiovascular, gastrointestinal, kidney, genitourinary, musculoskeletal, nervous system, oral, breast, periodontal, or skin cell or progenitor thereof. The shear modulus of the cell culture substrate of the device is in the range of the tissue type to be evaluated. Moreover, cell behavior or response are induced by contact with substrates of varying stiffness. For example, the differentiation path of stem or progenitor cells is driven toward a certain phenotype based on the shear modulus of the substrate upon which the cells are cultured.

BRIEF DESCRIPTION OF THE FIGURES

FIG. 2 is a flowchart and illustrative view of a method and apparatus for creating compliant substrates with two polymerization solutions.

FIG. 4 is a flowchart and illustrative view of method and apparatus for creating compliant substrates with a single polymerization solution.

FIG. 9 includes graphs comparing the cell growth of different cell types as a function of the shear modulus values of the hydrogels the cell are grown on.

DETAILED DESCRIPTION OF PREFERRED EMBODIMENTS

Cells grown on rigid plastic behave differently than the same cells residing in soft tissues. For example, rigid substrates can typically support high rates of proliferation, but also tend to attenuate cell differentiation, which can distort the normal function of cells in their native environment. Accordingly, the inventions described herein provide for growing cells on substrates that mimic the elasticity of soft tissues and offers an approach that will capture a fundamental aspect of the tissue environment while retaining the simplicity of in vitro systems.

Embodiments of the invention provide techniques for fabricating hydrogels with elastic properties covering a broad, physiologically relevant range. Glass-bottomed multi-well plates can be used. Cells can be studied in an appropriate elastic environment. A multi-well plate can use synthetic matrix-coated hydrogels to span a physiological range of shear modulus values. For example, a 96-well plate, which is a generally used format for biological assays, can be used. The system can also be extended to other formats that are amendable to high-throughput screening (384-well plates) or cell cultivation (petri dish). In general, to replicate soft tissue elasticity, a polyacrylamide hydrogel is polymerized as a thin, optically transparent layer which is affixed to the bottom of each well. By controlling the number of crosslinks that interconnect the hydrogel network, the elasticity can be tuned over the range of typical soft tissues (heart, lung, kidney, liver, muscle, neural, etc.) from elastic modulus ~20 Pascals (fat) to ~100,000 Pascals (skeletal muscle). In comparison, prior art cell culture dishes made from polystrene plastic have a stiffness of ~3,000,000,000 Pascals.

Figure 1:
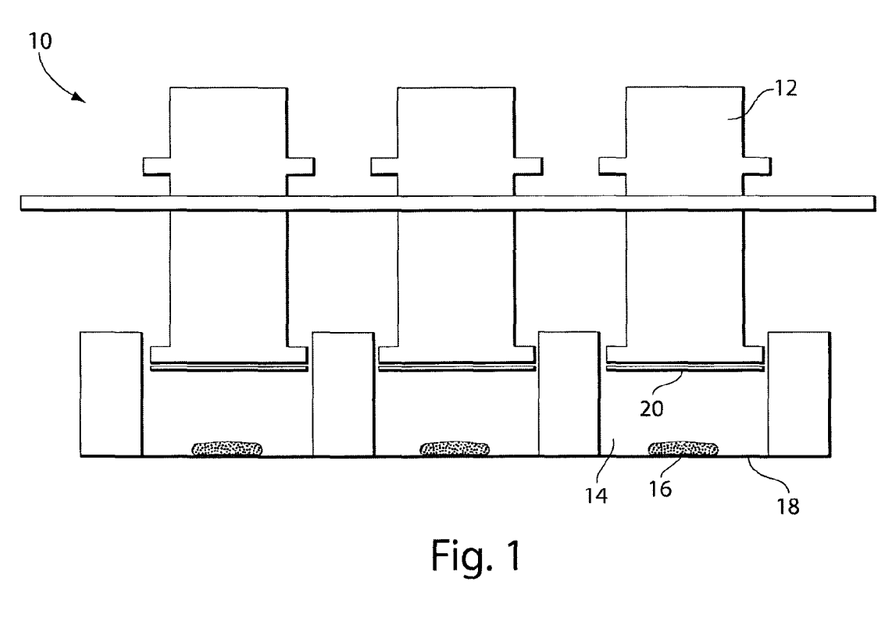
FIG. 1 is a side view of an assembly for fabricating hydrogels.

Referring to FIG. 1, an assembly for fabricating hydrogels 10 is shown. The assembly 10 includes at least one peg 12, a well 14, a polymerization solution 16, a glass well bottom 18, and a glass plate 20. The well 14 can be a multi-well configuration such as a 96-well assembly comprising a 12×8 matrix of wells in a plate (e.g., a Matrical 96-well assembly). The well 14 can also be a 6-well, 24-well, 384-well configurations. Generally, the well 14 can include standard multi-well plates used to study various biological endpoints under different interventions. The bottom of the well bottom 18 can be glass to allow for observation of cells placed within the well 14. The well bottom 18 can be other material configured to inhibit oxygen from flowing into the polymerization solution 16. In an embodiment, the polymerization solution 16 can be comprised of variable ratios of acrylamide:bis-acrlamide, and can be delivered into the well via a dispensing system (e.g., pipette, automated liquid dispensing system). The polymerization solution 16 can be polymer hydrogels such as polyalkylimide, poly(N-vinyl formamide), polyvinyl alcohol, poly(ethylene glycol). Also, polydimethylsiloxane, silicone, glycosaminoglycans, hyaluronic acid, chondroitin sulfate, polysaccharide, self-assembling peptides, collagen, gelatin, fibrin, methylcellulose, agarose. For a 384-well assembly, each well can typically receive 1-2 micro liters of polymerization solution 16. A 96-well assembly typically will receive about 5 micro liters. The amount of polymerization solution can change based on the desired thickness of resulting gel. The delivery system can be a pipette or similar liquid dispensing system (e.g., BioTek Microplate Liquid dispensing system). The glass plate 20 can be hydrophobic glass, and is disposed at the distal end of the peg 12. As an example, and not a limitation, a circular well 14, the diameter of the glass plate 20 is less than the diameter of the well 14. The well 14, peg 12, well bottom 18, and glass plate 20 can be other shapes.

In operation, the peg 12 can be lowered and raised within the well 14 such that the glass plate 20 can contact the polymerization solution 16. For example, the glass plate 20 can be disposed within 50 microns of the well bottom 18 such that the polymerization solution 16 is compressed to a uniform thickness across the diameter of the well 14. The glass plate 20, however, need not be a uniform surface. The plate 20 can include positive and negative designs (e.g., bumps, dimples, holes) to create creases and other irregularities in the surface of the polymerization solution 16. The well 14 and peg 12 can be coupled to linear and rotary actuators such that they can be moved independently, for example, to present the well 14 to a dispensing system, to place the well 14 under the peg 12, and to move the bottom of the well 18 and the glass plate 20 closer together.

Referring to FIG. 2, with further reference to FIG. 1, a method and apparatus for creating compliant substrates 100 is shown. The process 100, however, is exemplary only and not limiting. The process 100 may be altered, e.g., by having stages added, removed, or rearranged.

At stage 102, a polymerization solution 16 is placed into a well. As an example and not a limitation, each well of a 384-well tray contains approximately 1-2 µl of a polymer hydrogel. For example, an acrylamide/bis-acrylamide mixture can be used. Different concentrations of the acrylamide/bis-acrylamide mixture can be used to produce gels of different shear modulus, for example, ranging from 20 to 100,000 Pa. Other polymer hydrogels such as polyalkylimide, poly(N-vinyl formamide), polyvinyl alcohol, poly(ethylene glycol), polydimethylsiloxane, silicone, glycosaminoglycans, hyaluronic acid, chondroitin sulfate, polysaccharide, self-assembling peptides, collagen, gelatin, fibrin, methylcellulose, and agarose can be used. The shear modulus of the gels in each well 14 need not cover a range. In an embodiment, a multi-well tray can include gels with a standard shear modulus (e.g., 5000, 10,000, 17,000 Pa) in each well.

At stage 104, the relative position between the peg 12 and the well 14 is changed such that the glass plate 20 contacts the polymerization solution 16. As an example, and not a limitation, the polymerization solution 16 is compressed to thickness of less than 50 microns. The glass plate 20 remains in contact with the polymerization solution 16 for approximately 5-10 minutes. Thicker gels may require longer set-up time.

Figure 3:
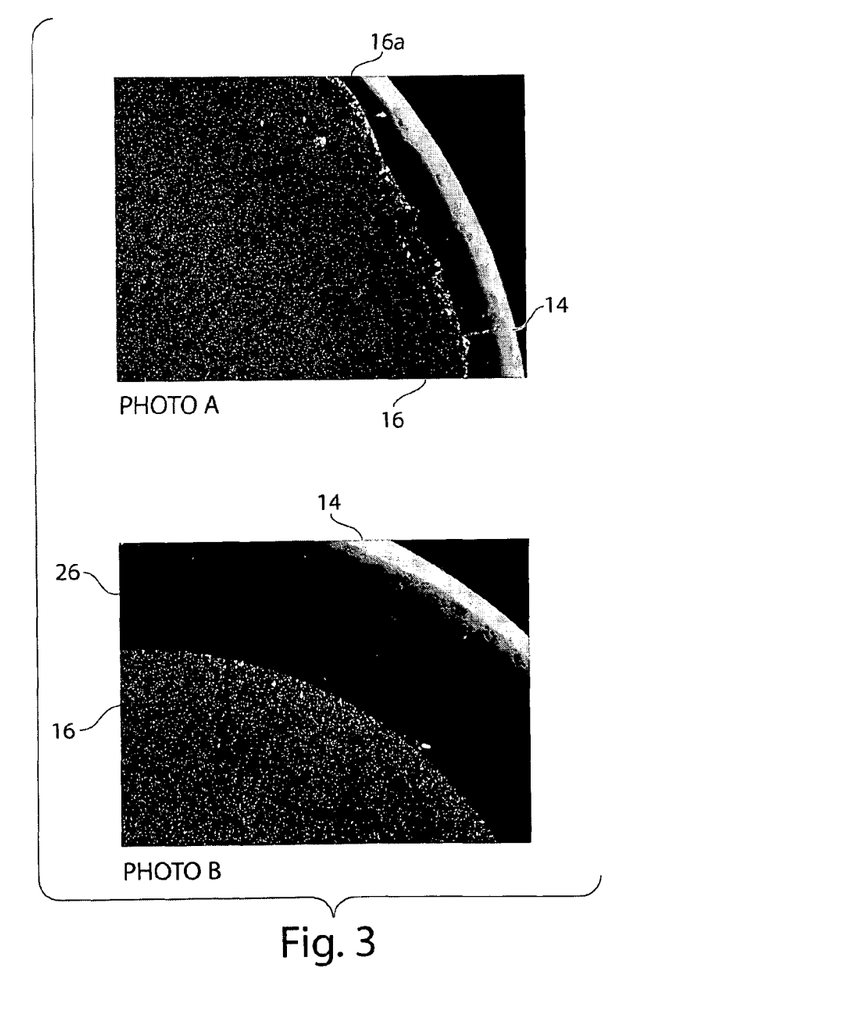
FIG. 3 are photographs of edge effects of a polymer surface.

At stage 106, the polymerization solution 16 may not completely polymerize at the wall of the well 14 due to oxygen inhibition. In general, polymerization relies on a free radical generating system and hence can be susceptible to other factors. For example, oxygen is a free radical trap, and surfaces which absorb or are permeable to oxygen will inhibit polymerization, which can result in localized gel distortions or unpolymerized gel. Accordingly, as the peg 12 and glass plate 20 are removed at stage 108, a non-polymerized area 16a may exist. Referring to Photo A in FIG. 3, the non-uniform edge of the polymerization solution 16 is shown in relation to the gaps 16a and the well wall 14.

At stage 110, the polymerization solution 16 (i.e., gel) is functionalized via conjugation with a ligand. The surface ligand 22 is generally added to improve cell adhesion to the gel 16. For example, the gel 16 surfaces are treated with a heterobifunctional crosslinker (e.g., sulfo-SANPAH), which can covalently link a desired ligand to the gel. Other heterobifunctional crosslinkers such as amine-reactive photoreactive (e.g., NHS/nitrophenyl azide crosslinkers: ANB-NOS, sulfo-SBED), amine-carboxyl reactive, amine-sulfhydryl reactive, and acrylic acid esters, can be used. Exemplary ligands include extracellular matrix (ECM) proteins such as collagen (type I collagen), laminin, fibronectin or combinations thereof. Other cell attachment ligands/promoters such as collagen (type III, IV), vitronectin, poly-d-lysine, cyclic and linear RGD peptides, peptide sequences, and negatively or positively charged groups, can be used. As an example, and not a limitation, the surface of the gel 16 can be activated by adding approximately a solution containing 1 mM sulfosuccinimidyl-6-(4-azido-2-nitrophenylamino) hexanoate dissolved in 200 mM HEPES. The dishes can be exposed to ultraviolet light for 5 minutes, washed twice with 0.1M HEPES solution, washed once with PBS, coated with type I Collagen solution (0.1 mg/ml) and stored overnight at 4° C. On the following day, the gel 16 can be washed, hydrated with a serum free media solution and stored in an incubator at 37° C. and 5% $CO_2$. A 96-well plate, for example, can be loaded with plurality of polymerization solutions 16 in different wells. The wells can be covered by an array of pegs 14 and plates 20 and cured simultaneously to produce gels 16 of uniform thickness and various shear moduli (e.g., 100, 200, 400, 800, 1600, 3200, 6400, 12800, 25600, and 51200 Pa).

At stage 112 a second polymerization solution 26 can be added via a delivery system 24. The delivery system 24 can be a pipette, or similar liquid dispensing system. The second polymerization solution 26 can be used to overcome the edge effect caused by oxygen inhibition (i.e., 16a). In general, the second polymerization solution 26 is a softer polyacrylamide (i.e., a relatively elastic polymer) which can adhere to the well.

At stage 114, a meniscus can be formed by tapping the well 14 to distribute the second polymerization solution 26 evenly. The tapping can be performed by a mechanical tapper or manually. At stage 116, oxygen in the air inhibits polymerization at the interface between the air and the second polymerization solution 26. That is, polymerization occurs only at the gel/well edge, where the depth of the meniscus is the greatest. At stage 118, a uniform circular boarder is formed around the well 14. The ring of second polymerization solution 26 assists in affixing (i.e., holding in place) the functionalized gel 16 in the well. Also, the second polymerization solution 26 can be non-functionalized (and soft) which can minimize cell attached an growth on the ring 26. Referring to Photo B of FIG. 3, a photograph of a uniform edge of the first polymerization solution 16 as outlined by the second polymerization solution 26 is shown.

Acrylamide, and other polymer solutions, can be highly toxic to cells, so it is generally necessary to include a detoxification process. At stage 120, glutathione 32 can be added to detoxify free, unpolymerized acrylamide. For example, a solution of glutathione 32 can be dispensed into the well 14 and incubated for several hours prior to seeding the well 14 with cells.

In another embodiment, an assay may include cells that are particularly sensitive to the second polymer solution used in process 100, and the cleaning at stage 120 may be insufficient to detoxify the well 14 to a required level. Referring to FIG. 4, with further reference to FIGS. 1 and 2, a method and apparatus for creating compliant substrates 200 with a single polymer solution is shown. The process 200, however, is exemplary only and not limiting. The process 200 may be altered, e.g., by having stages added, removed, or rearranged.

The method and apparatus 200 can include a multi-well pin block 201 comprising a plurality of pin assemblies 210 operably connected to a plurality of glass plates 20. The dimensions of each of the glass plates a slightly less than the dimensions of each of the wells 14 on a multi-well plate, such that a glass plate 20 can be disposed within a well 14. In an embodiment, the multi-well plate can be a 96-well plate from Matrical, Inc., that uses a non-cytotoxic adhesive to bind the glass bottom 18 to well. Typically, the glass thickness is compatible with fluorescence-based assays, as well as high power and confocal microscopy (i.e., at thickness of about 170 microns).

At stage 220, a multi-well pin block 201 can be assembled and cleaned. The pin block glass 20 can be treated with a hydrophobicizing agent (e.g., Surfasil, Pierce), and cleaned thoroughly with methanol prior to gel casting. In an embodiment, the thickness of the gel can be controlled by placing a spacer on each of the four corners of the plate 20.

At stage 222, each of the wells 14 of a multi-well plate can be treated with 50 micro-liters of an aqueous solution of silane to ensure the subsequently added polymer solution will be affixed to the well. In general, the well 14 is treated with agent which can be a substituted propyl-trimethoxysilane of the formula:

where
R is $NR^1R^2$ or $OR^3$
$R^1$ and $R^2$ are independently hydrogen or $C_1$-$C_6$ alkyl;
$R^3$ is alkyl, alkenyl, alkynyl or acyl (e.g., $C(O)R^4$, where R4 is hydrogen, alkyl, alkenyl, or alkynyl).
Certain Compounds Include 3-aminopropyltrimethoxysilane 3-methacryloxypropyltrimethoxysilane For example, for polyacrylamide hydrogels, a solution of approximately 0.004-0.4% 3-methacryloxypropyltrimethoxysilane can be placed in the well 14 for approximately 10 minutes. At stage 224, each of the wells 14 is rinsed in distilled water and dried (e.g., the entire multi-well plate can be placed distilled water and air or blown dry). The treated glass surface 18 reacts with subsequently added polyacrylamide to from a covalent, long-lasting bond which affixes the polyacrylamide to the well.

In an embodiment, at stage 222, each of the wells of a multi-well plate can be treated with 3-aminopropyltrimethoxysilane. For example, for polyacrylamide hydrogels, a well can be coated with a solution of approximately 97% 3-aminopropyltrimethoxysilane for approximately 10 minutes. At stage 224, each of the wells is rinsed in distilled water and dried (e.g., the entire multi-well plate can be placed in distilled water and air or blown dry). The treated glass surface is then coated with 0.5% glutaraldehyde in water for 30 minutes and then rinsed and dried. The fully functionalized glass reacts with subsequently added polyacrylamide to form a covalent, long-lasting bond which affixes the polyacrylamide to the well.

At stage 226, a small amount (e.g., approximately 5 microliters for each well in a 96-well tray) of polymerization solution 16 is added to the bottom of each well 14. As an example, and not a limitation, the polymerization solution 16 can be mixture of acrylamide and bisacrylamide. Other polymerization solutions as discussed above with the respect to the process 100 may also be used. The ratio of acrylamide and bisacrylamide can vary based on the desired stiffness of the completed hydrogel. The mixture may also contain 0.15% TEMED, 0.075% ammonium persulfate, and 1 mM sodium bisulfite (which acts as an oxygen scavenger).

At stage 228, the multi-pin array block 201 is aligned over the multi-well tray such that the each well 14 receives a pin and glass assembly 210, 20. In an embodiment, the multi-pin array block can be constructed with a second multi-well tray, where each well is affixed to a rod and glass plate assembly 210, 20, such that the ends of the rods that are affixed to the glass plate extend out of the second multi-well tray. In operation, the second multi-well tray can be inverted and aligned over the multi-well tray that contains the polymerization solution 16, such that the glass plates 20 can be lowered into the wells 14.

At stage 230, the glass plate 20 is pressed firmly against the polymerization solution 16 and the glass bottom 18. As an example, and not a limitation, the thickness of the solution 16 (i.e., gel) after compression can be less than 100 microns (e.g., 10, 25, 50, 70, 80 microns). Depending on the assay, the thickness of the gel 16 can also be larger (e.g., 0.3, 0.5, 0.75, 1.0 mm). The volume of polymer solution added can impact the thickness of the resulting gel. The glass plate 20 remains in position until the solution 16 is completely polymerized (e.g., approximately 10-15 minutes, but longer time may be required for thicker gels). In an embodiment, the multi-well tray and pin-array assemblies can be placed in an anoxic chamber. For example, an nitrogen environment.

At stage 232, the glass plate 20 is removed from the well 14. Typically, the plate 20 is removed by lifting while applying a lateral force such that plate 20 peels off of the gel 16. Once the plate 20 is removed from each of the wells 14, approximately 100 micro liters of distilled water 212 is added to the well to allow the gel 16 to hydrate.

At stage 234, the distilled water 212 is removed and the gel 16 is derivatized with a heterobifunctional crosslinker, and then a ligand. In an embodiment, 35 micro liters of 0/5 mg/ml Sulfo-SANPAH (N-Sulfosuccinimidyl-6-[4'-azido-2'-nitrophenylamino]hexanoate) in 50 mM HEPES buffer is added to each well 14 (i.e., for a well in a 96-well tray). The wells 14 can then be exposed to UV light for approximately 5 minutes. After exposure to the UV light, the sulfo-SANPAH solution can be removed, and the gels 16 can be rinsed with 100 micro liters of 50 mM HEPES. 100 micro liters of 100 ug/ml collagen I (pepsin-solubilized) in PBS can then be added to each well, and then incubated from approximately 4 hours at room temperature. The collagen I solution is then removed from the wells. Other crosslinkers and ligands as discussed above in relation to the process 100 can be used. In an embodiment, the polymerization solution 16 can be derivatized prior to being added to the well 14.

At stage 236, the wells 14 and gel 16 is sterilized. In an embodiment, 200 micro liters of PBS is added to each well 14. The wells 14 are then sterilized for approximately 2 hours under UV light 216. The PBS is removed, and cells can be seeded in approximately 200 micro liters of media.

Figure 5:
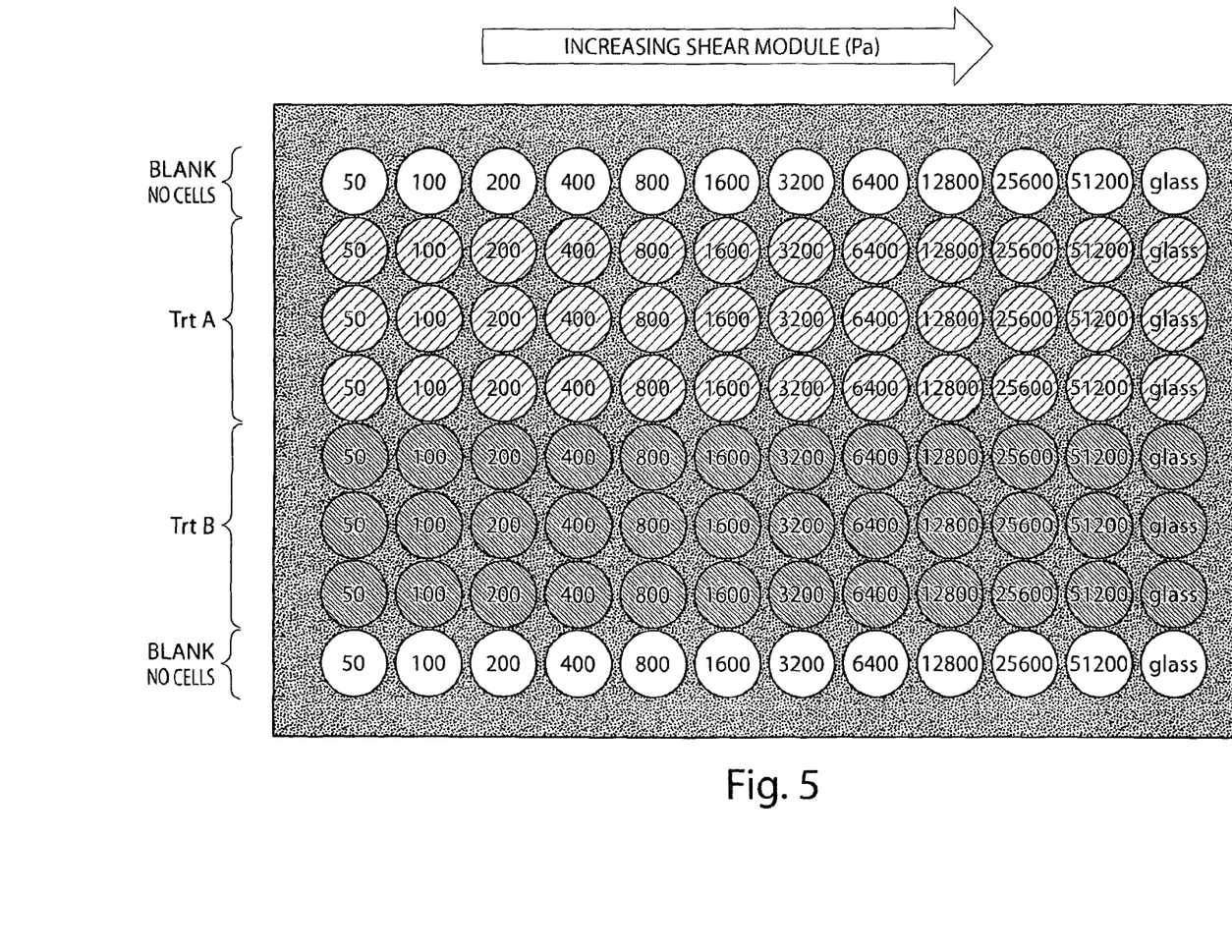
FIG. 5 is an exemplary 96-well plate configured with a plurality of gels.

Referring to FIG. 5, with further reference to FIGS. 2 and 4, in an embodiment, a 96-well plate can be configured so the shear modulus of the elastic gel 16 in each of the wells 14 varies columnwise. For example, the well columns can be loaded with gels 16 of increasing shear modulus in ascending order (i.e., 50, 100, 200, 400, 800, 1600, 3200, 6400, 12800, 25600 and 51200 Pa respectively). Further, a non-derivatized gels can serve as a background control for each shear modulus value. The rows of the plate can include different test cells and blanks as required for a test protocol. In an embodiment, the shear modulus values of the gels throughout a multi-well plate can be substantially similar. For example, for an assay in which shear modulus is consistent in the wells, and cell types vary.

Figure 6:
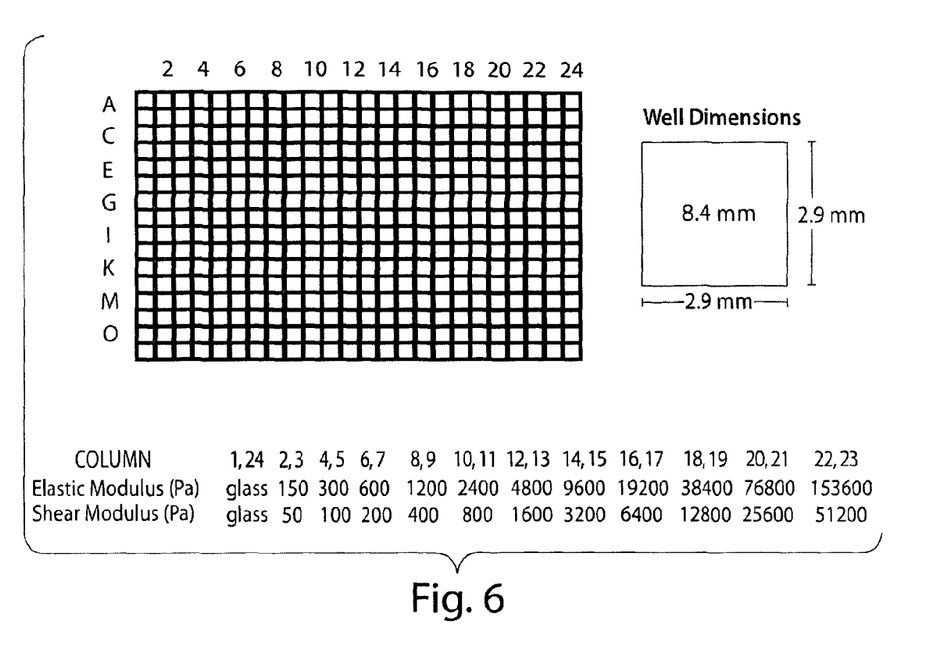
FIG. 6 is an exemplary 384-well plate configured with a plurality of gels.

Referring to FIG. 6, with further reference to FIGS. 2 and 4, in an embodiment, a 384-well plate can be configured so the elastic modulus and the shear modulus of the elastic gel 16 in each of the wells 14 varies columnwise. For example, the gel 16 can have an elastic modulus of 150, 300, 600, 1200, 2400, 4800, 9600, 19200, 38400, 76800, and 153600 Pa, and a shear modulus of 50, 100, 200, 400, 800, 1600, 3200, 6400, 12800, 25600 and 51200 Pa.

Figure 7:
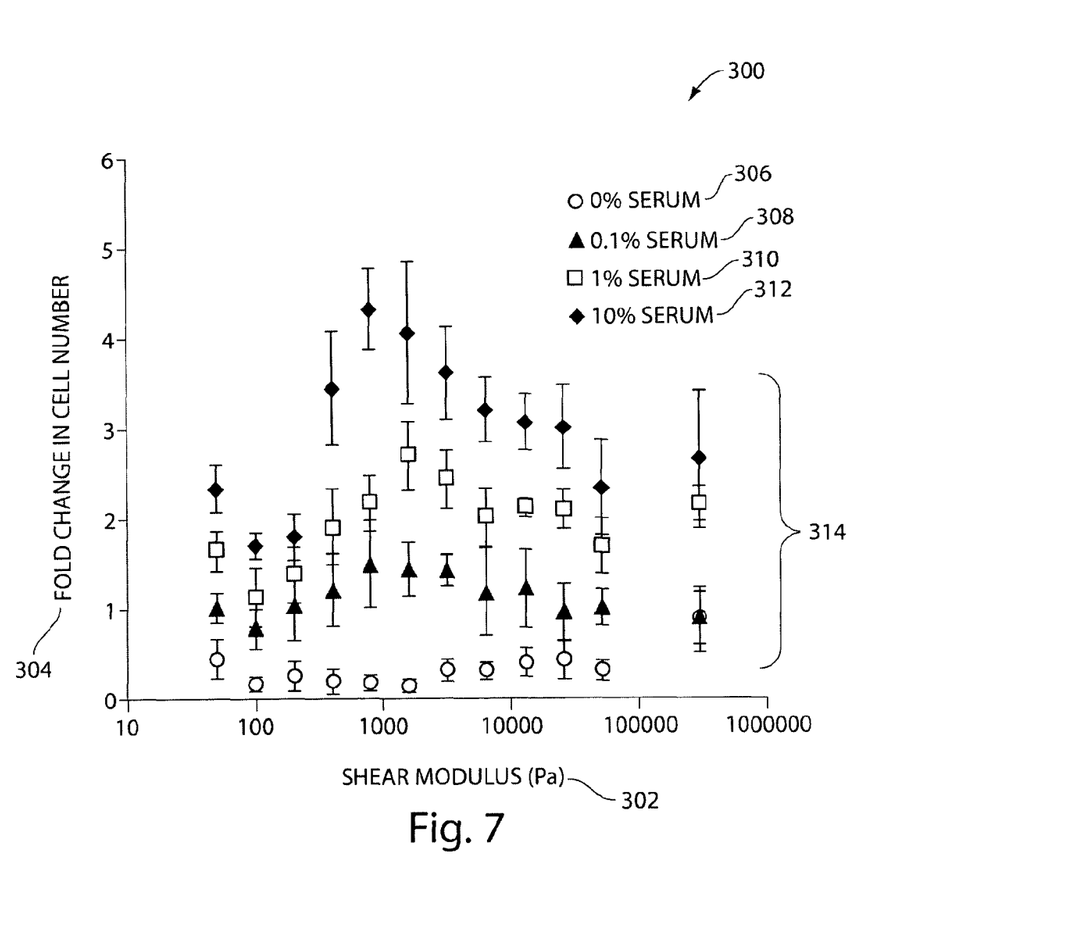
FIG. 7 is a graph depicting human lung fibroblast cell growth in a 384-well plate containing hydrogels with a range of shear modulus values.

Referring to FIG. 7, with further reference to FIGS. 2, 4 and 6, a graph depicting human lung fibroblast cell growth in a 384-well plate containing hydrogels 16 with a range of shear moduls values is shown. The graph includes an x-axis 302 representing the shear modulus of the gels which the cells were grown. The scale of the x-axis 302 is logarithmic and ranges from 10 to 1,000,000 Pascal (Pa). The y-axis of the graph 304 represents the fold change in cell number (i.e., 2-fold, 3-fold) and has a range from 0 to 6-fold. Four groups of data are plotted on the graph 300, including 0% serum 306, 0.1% serum 308, 1% serum 310, and 10% serum 312. The results plotted on the graph 300 are based on adult human lung fibroblasts (CCL-151) that were seeded in 384-well plates containing gels of different shear modulus values, and exposed to the indicated serum concentrations for a period of 48 hours. The results demonstrate that the number of cells increased at intermediate shear modulus, peaking at approximately 800 Pa. The right-most data points 314 represents cells grown on a rigid glass substrate.

Figure 8:
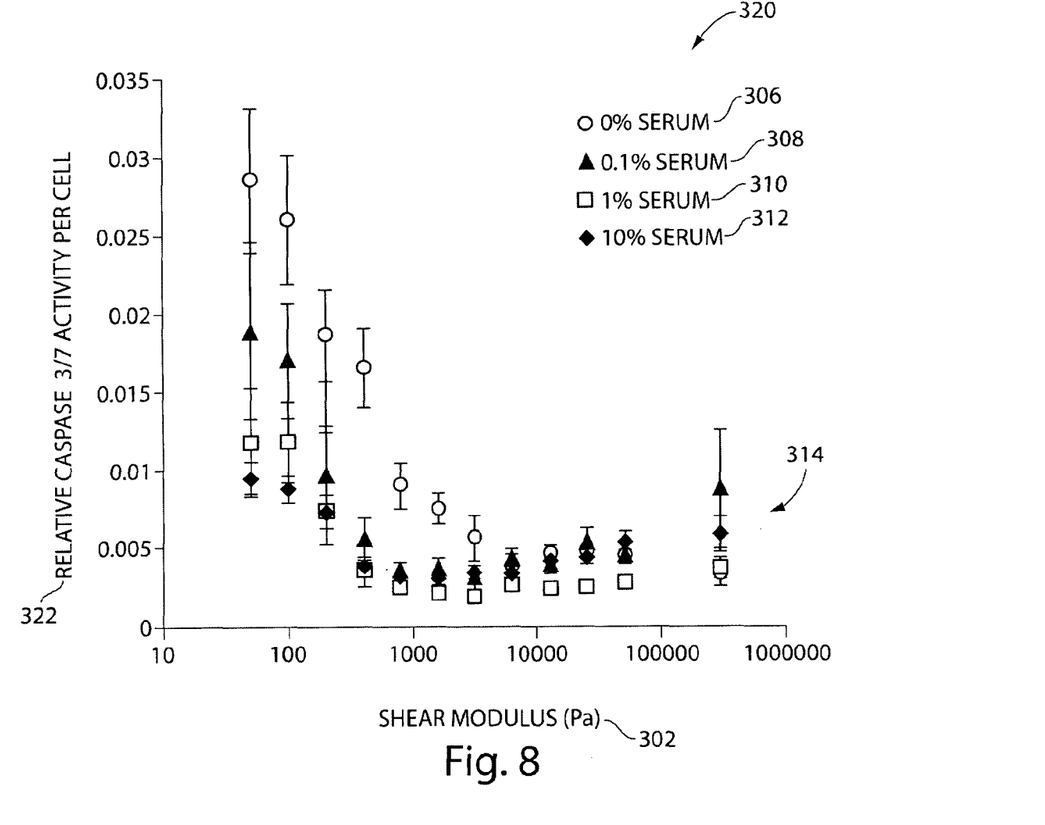
FIG. 8 is a graph depicting apoptosis in human lung fibroblast grown in a 384-well plate containing hydrogels with a range of shear modulus values.

Referring to FIG. 8, with further reference to FIGS. 2, 4 and 6, a graph 320 depicting apoptosis in human lung fibroblast grown in a 384-well plate containing hydrogels 16 with a range of shear modulus values is shown. The graph includes an x-axis 302 representing the shear modulus of the gels which the cells were grown. The scale of the x-axis 302 is logarithmic and ranges from 10 to 1,000,000 Pascal (Pa). The y-axis of the graph 322 represents the relative caspase 3/7 activity per cell and has a range from 0 to 0.035. Four groups of data are plotted on the graph 300, including 0% serum 306, 0.1% serum 308, 1% serum 310, and 10% serum 312. The results plotted on the graph 320 are based on adult human lung fibroblasts (CCL-151) that were seeded in 384-well plates containing gels of different shear modulus values, and exposed to the indicated serum concentrations for a period of 48 hours. The results demonstrate that caspase 3/7 activity, a marker of apoptosis, is elevated in cells grown on softer gels. The effect is potentiated when cells are grown in serum-free media. The right-most data points 314 represents cells grown on a rigid glass substrate.

Figure 9:
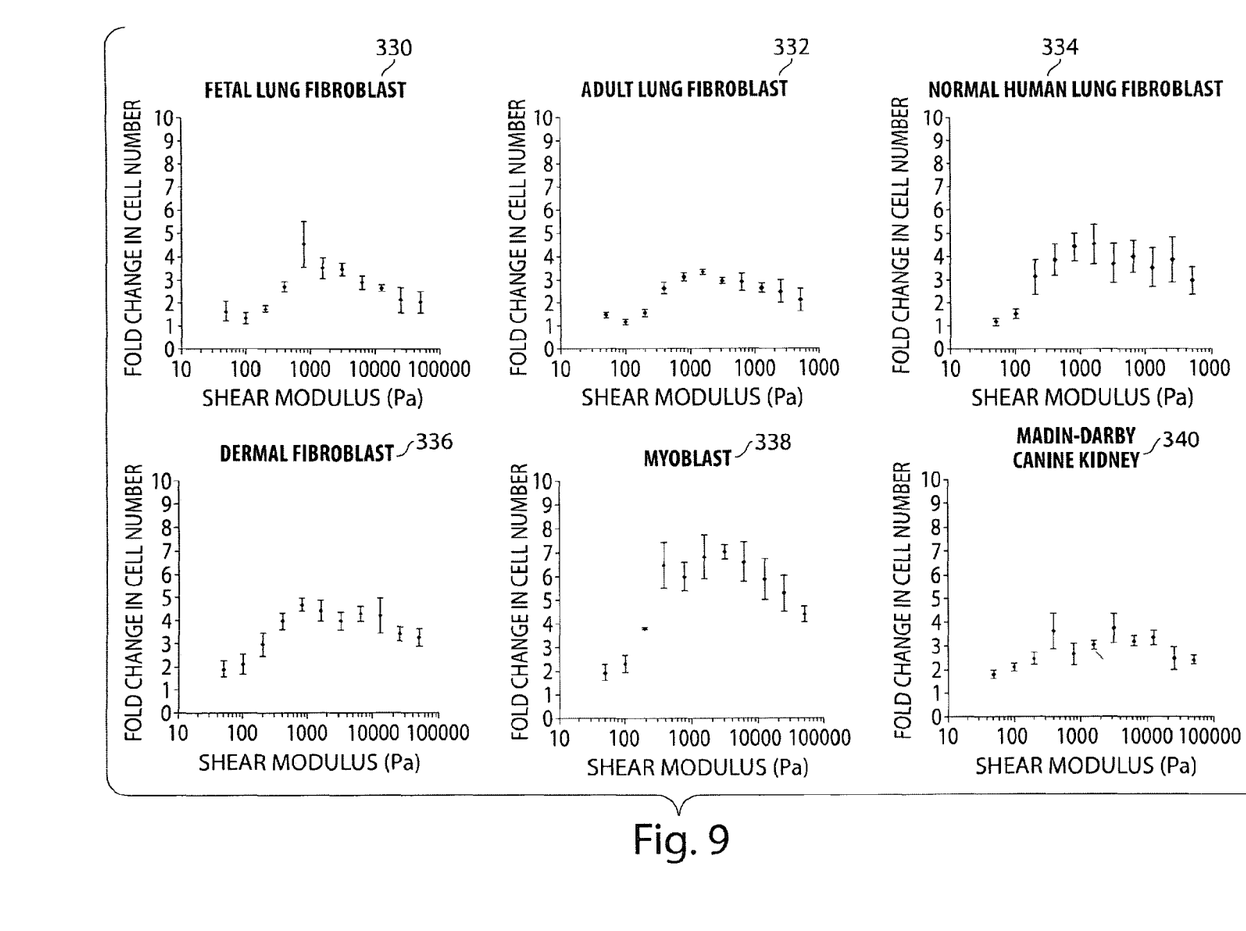

Referring to FIG. 9, with further reference to FIGS. 2, 4 and 6, graphs 330, 332, 334, 336, 338, 340 comparing the cell growth of different cell types as a function of the stiffness of the hydrogels 16 the cell are grown on are shown. Each of the graphs includes an x-axis representing the shear modulus of the gels which the cells were grown. The scale of the x-axis is logarithmic and ranges from 10 to 1,000,000 Pascal (Pa). The y-axis of the graphs represents the fold change in cell number (i.e., 2-fold, 3-fold) and have a range from 0 to 10-fold. The cells were seeded at a density of 100 cells/sq mm in 384-well plates and cultured for 48 hours in media containing 10% serum. The cells include fetal lung fibroblast 330, adult lung fibroblast 332, normal human lung fibroblast 334, dermal fibroblast 336, myoblast 338 and Madin-Darby canine kidney 340. The results indicate that the change in cell number is based on shear modulus and the cell type.

A compliant surface multi-well culture plate can be considered an upgrade to conventional 2-D cell cultures. In general, the compliant surface multi-well culture plate can meet the a needs for more realistic cell culture. For example, researchers have demonstrated that mesenchymal stem cell differentiation along different lineages can be accomplished simply by tuning extracellular stiffness. The compliant surface multi-well culture plate technology can be used to screen for a differentiation stiffness, and once identified, would serve as the substrate for all future studies. Further, mechanical and biochemical factors can be assessed in a combinatorial fashion to create a powerful discovery matrix.

Simulation of Physiological Conditions

Most drug screens, particularly those for cancer, are performed with cells plated on rigid multi-well plates. There a number of chemotherapeutic drugs, however, which fail to inhibit proliferation on rigid plates, but succeed on soft substrates; there are examples of the reverse as well. In general, the knowledge of what mechanical properties (i.e., elastic modulus) will evoke a desired cell phenotype can be of tremendous value to tissue engineers in their design of 3-D scaffolds for tissue engineering.

The compliant surface multi-well culture plate can also be used for disease-based research. In general, there is distinct stiffening (or softening) of tissue that can occur in a number of diseases, such as sclerodoma, atherosclerosis, emphysema, and fibrosis of the lung, liver and kidney. The compliant surface multi-well culture plate technology opens up the field to the assessment of stiffness-dependent cell behaviors at a level of detail that is not currently possible. For example, simulation of cell growth/behavior to contact with fat tissue is carried out by growing cells on a surface characterized by a shear modulus of fat (approximately 10 Pascal). Different tissue types are characterized by different stiffness, e.g., normal brain tissue has a shear modulus of approximately 200 Pascal. Cell growth/behavior also differs relative to the disease state of a given tissue, e.g., the shear modulus of normal mammary tissue is approximately 100 Pascal, whereas that of breast tumor tissue is approximately 2000 Pascal. Similarly, normal liver tissue has a shear modulus of approximately 300 Pascal compared to fibrotic liver tissue, which is characterized by a shear modulus of approximately 800 Pascal. Growth, signal transduction, gene or protein expression/secretion, as well as other physiologic parameters are altered in response to contact with different substrate stiffness and evaluated in response to contact with substrates characterized by mechanical properties that simulate different tissue types or disease states.

Differentiation of stem cells is influenced by mechanical properties of the culture substrate. For example, stem cells, e.g., mesenchymal stem cells, cultured on a substrate with a shear modulus of approximately 300 Pascal induces differentiation to cells of a neurogenic phenotype. Stem cells exposed to an intermediate stiffness, e.g., 3000 Pascal, are induced to differentiate into myogenic tissue. In another example, stem cells grown on a substrate characterized by a relative stiff shear modulus (e.g., 10-15,000 Pascal) are induced to differentiate into cells with an osteogenic phenotype. Thus, substrates of varying stiffness described herein and devices containing those substrates are also useful to influence or drive differentiation of stem or progenitor cells toward one phenotype compared to a different phenotype based on contact with the mechanical properties of the Further, in phenotype-targeted cell culture, the general rigidity of plastic is an extreme condition that can induce cell phenotypes that may be undesirable, or not prevalent in native environments. The compliant surface multi-well culture plate technology can be particularly suited for the culture of neurons, which exhibit increased branching and growth on soft substrates.

While the description above refers to the invention, the description may include more than one invention.

What is claimed is:

1. An apparatus comprising:
a multi-well plate;
a first gel affixed in at least a first well in the plate; and
a second gel affixed in at least a second well in the plate, wherein the shear modulus of the first and second gels differ by 50 Pascals to 25600 Pascals.

2. The apparatus of claim 1 comprising a third gel disposed in at least a third well of the plate, wherein the shear modulus of the third gel is different from the shear modulus of the first and second gels.

3. The apparatus of claim 1 wherein the wells are disposed on the plate in columns and the shear modulus of the gels in the wells in a column is the same.

4. The apparatus of claim 1 wherein the multi-well plate is a 96 well plate.

5. The apparatus of claim 4 wherein the plate includes 12 columns of wells such that one column of wells is empty and 11 columns of wells contain gels, whereby the gels of wells of a column of the 11 columns have the same shear modulus.

6. The apparatus of claim 1, wherein the thickness of the first gel is less than 1 millimeter.

7. The apparatus of claim 1, wherein the thickness of the first gel is less than 100 microns.

8. The apparatus of claim 1, wherein the thickness of the second gel is less than 1 millimeter.

9. The apparatus of claim 1, wherein the thickness of the second gel is less than 100 microns.

10. The apparatus of claim 1, wherein at least one of the first gel and second gel is derivatized with a heterobifunctional crosslinker and a ligand.

11. The apparatus of claim 1, wherein the plate comprises 6, 12, 24, 96, or 384 wells.

12. The apparatus of claim 1, wherein the plate comprises a glass bottom.

13. The apparatus of claim 1, wherein at least one of the first gel and the second gel is a hydrogel.

14. The apparatus of claim 13, wherein the at least one of the first gel and the second gel is a polyacrylamide hydrogel.

15. The apparatus of claim 13, wherein the at least one of the first gel and the second gel comprises material selected from the group consisting of polyacrylamide, polyalkylimide, poly(N-vinyle formamide), polyvinyl alcohol, polyethylene glycol), polydimethylsiloxane, silicone, glycosaminoglycans, hyaluronic acid, chondroitin sulfate, polysaccharide, self-assembling peptides, collagen, gelatin, fibrin, methylcellulose, and agarose.

16. The apparatus of claim 15, wherein the at least one of the first gel and the second gel is comprised of a toxic material, which has been subject to a detoxification process.

* * * * *

UNITED STATES PATENT AND TRADEMARK OFFICE
CERTIFICATE OF CORRECTION

PATENT NO. : 8,871,499 B2  
APPLICATION NO. : 12/675839  
DATED : October 28, 2014  
INVENTOR(S) : Tschumperlin et al.

Page 1 of 1

It is certified that error appears in the above-identified patent and that said Letters Patent is hereby corrected as shown below:

In the Specification

Delete the paragraph beginning at Column 1, Line number 16 and replace it with the following paragraph:
This invention was made with government support under HL082856, GM073628, and HL088028 awarded by the National Institutes of Health. The government has certain rights in the invention.

Signed and Sealed this
Twenty-first Day of January, 2025

Coke Morgan Stewart
*Acting Director of the United States Patent and Trademark Office*